US009509930B2

(12) United States Patent
Wany

(10) Patent No.: US 9,509,930 B2
(45) Date of Patent: Nov. 29, 2016

(54) DEVICE COMPRISING A SET OF ELECTROMAGNETIC RADIATION SENSITIVE DETECTORS AND ARRANGEMENT OF A SET OF SUCH DEVICES

(71) Applicant: AWAIBA HOLDING S.A., Yverdon-les-Bains (CH)

(72) Inventor: Martin Wany, Yverdon-les-Bains (CH)

(73) Assignee: Awaiba Holdings S.A., Yverdon-les-Bains (CH)

( * ) Notice: Subject to any disclaimer, the term of this patent is extended or adjusted under 35 U.S.C. 154(b) by 0 days.

(21) Appl. No.: 14/412,215

(22) PCT Filed: Jul. 10, 2013

(86) PCT No.: PCT/CH2013/000123
§ 371 (c)(1),
(2) Date: Apr. 16, 2015

(87) PCT Pub. No.: WO2014/008615
PCT Pub. Date: Jan. 16, 2014

(65) Prior Publication Data
US 2015/0229860 A1    Aug. 13, 2015

(30) Foreign Application Priority Data

Jul. 10, 2012  (CH) ..................... 1062/12

(51) Int. Cl.
*H01L 27/14*  (2006.01)
*H04N 5/378*  (2011.01)
(Continued)

(52) U.S. Cl.
CPC ............. *H04N 5/378* (2013.01); *A61B 1/042* (2013.01); *A61B 6/4233* (2013.01);
(Continued)

(58) Field of Classification Search
CPC .... H04N 5/378; H04N 5/376; H04N 5/3696; H04N 2005/2255; H01L 27/14609; H01L 27/14812; H01L 27/14634
See application file for complete search history.

(56) References Cited

U.S. PATENT DOCUMENTS 5,291,010 A    3/1994  Tsuji
7,009,645 B1   3/2006  Sandini et al.
(Continued)

FOREIGN PATENT DOCUMENTS

| EP | 1 255 401 A1 | 11/2002 |
| FR | 2 930 841 A1 | 11/2006 |
| JP | 2010-273757 A | 12/2010 |

OTHER PUBLICATIONS

International Search Report Corresponding to PCT/CH2013/000123 mailed Dec. 4, 2013.

*Primary Examiner* — Tony Ko
(74) *Attorney, Agent, or Firm* — Davis & Bujold PLLC; Michael J. Bujold

(57) ABSTRACT

An image sensor, in particular, for endoscopic applications or miniaturized surveillance cameras. The sensor includes a matrix of image points arranged to provide an image of an explored area of which the shape substantially corresponds to the geometry of the matrix. This sensor consists of a matrix of photodetector cells structured in rows and columns, orthogonal to one another, which has a polygonal shape of which the contour has at least five sides that form part of a closed line, with orthogonal edges and oblique edges. This provides a solution to position the column and row address elements which allows each photoconductive cell to be connected to a current or voltage readout circuit, along oblique edges, such that the space beyond the matrix of photodetector elements is not substantially increased along the oblique edges.

17 Claims, 5 Drawing Sheets

(51) Int. Cl.
*A61B 6/00* (2006.01)
*A61B 1/04* (2006.01)
*H01L 27/146* (2006.01)
*H01L 27/148* (2006.01)
*H04N 5/369* (2011.01)
*H04N 5/376* (2011.01)
*H04N 5/225* (2006.01)

(52) U.S. Cl.
CPC .. *H01L 27/14609* (2013.01); *H01L 27/14812* (2013.01); *H04N 5/3696* (2013.01); *H04N 5/376* (2013.01); *H01L 27/14643* (2013.01); *H01L 27/14831* (2013.01); *H04N 2005/2255* (2013.01)

(56) References Cited

U.S. PATENT DOCUMENTS

| | | |
|---|---|---|
| 2006/0027625 A1 | 2/2006 | Dockus et al. |
| 2006/0237625 A1* | 10/2006 | Caupain .............. H01L 27/1463 250/208.1 |
| 2009/0033777 A1 | 2/2009 | Ligozat et al. |
| 2010/0141820 A1* | 6/2010 | Chenebaux ....... H01L 27/14609 348/302 |

* cited by examiner

DEVICE COMPRISING A SET OF ELECTROMAGNETIC RADIATION SENSITIVE DETECTORS AND ARRANGEMENT OF A SET OF SUCH DEVICES

This application is a National Stage completion of PCT/CH2013/000123 filed Jul. 10, 2013, which claims priority from Swiss patent application serial no. 1062/12 filed Jul. 10, 2012.

FIELD OF THE INVENTION

The present invention concerns a device containing a set of electromagnetic radiation-sensitive detectors, specifically an image sensor, particularly for endoscopic applications or miniature surveillance cameras, said detector comprising a matrix of image points designed to furnish an image of an explored area that generally corresponds in shape to the geometry of said matrix, in which the detectors are addressed through an addressing scheme along lines and columns of said matrix so each cell of said cell matrix may be connected to at least one readout circuit placed on the periphery of said matrix, said device consisting of a matrix of photodetector cells structured along mutually orthogonal lines and columns, that is polygonal in shape and the outline of which comprises at least five sides within a closed line, with orthogonal edges and at least one oblique edge connecting two orthogonal edges, specifically a square or rectangular surface with cut corners, specifically at 45°, each photodetector cell of which is directly connected to a readout circuit using voltage or current by an addressing system along lines and columns.

It also concerns an arrangement comprising a set comprised of these devices.

BACKGROUND OF THE INVENTION

Normally a device of this type consists of a matrix of image points called pixels, rectangular in shape, and the integrated circuit of the sensor is also rectangular. However, for numerous endoscopic applications and other applications requiring a very small size sensor, this rectangular shape is not ideal because the rectangular shape fills only a portion of the circular surface that usually corresponds to the space available for the device. The field of vision covered by a lens, which is typically circular, does not correspond to the sensitive surface of the rectangular sensor and either it covers only a portion of the lens's field of vision, or a sensor is used with corners that extend beyond the field of vision covered by a circular lens.

Since the rectangular shape of the assembly of a set of photosensitive cells for capturing an image is often poorly adapted to space constraints, numerous solutions have been proposed to achieve better adapted detectors. For example, U.S. Pat. No. 7,009,645 proposes an image sensor with a circular arrangement of photosensitive cells. The photosensitive cells are addressed for sequential reading according to a polar coordinate addressing system along beams and in circles. This arrangement has two major flaws, as a result of which such an arrangement is seldom used. First, the spatial resolution of such an arrangement of photodetector cells is not uniform and increases towards the center, and although measures for reducing the impact of this have been proposed, no perfectly uniform resolution has been obtained. Second, the majority of algorithms for treating images and displaying images are based on the image points being arranged in lines and columns, therefore it is imperative for such a sensor to convert to this image presentation format, requiring very burdensome calculations in order to transform space coordinates.

One known image sensor comprises a matrix of photosensitive elements whose individual signals are queued in a sequential process by addressing lines and columns of said photosensitive elements. This sequential addressing is achieved using a line addressing circuit placed along a peripheral edge of the matrix and a column addressing circuit which is along the other peripheral edge of the matrix.

Such a device works well when the sensor is square or rectangular in shape so that the addressing of lines and columns defines the image points without any overlap. For polygonal shapes, for example, simple addressing where each image point has a unique line address and a unique column address is not possible with only one of the elements, either line addressing or column addressing, placed along a peripheral edge of the device when the polygon does not contain at least a minimum of one rectangular angle, because in that case, at least along one side of the polygon, the line decoder and the column decoder must be placed at the same time.

Solutions using arrangements of photoelectric cell matrices with one or two corners cut off, for example as shown in U.S. Pat. No. 5,291,010 have been proposed, but the line addressing circuits and the column addressing circuits remain respectively on individual sides of the polygon.

Particularly in the field of CCD type detectors for intraoral X-ray radiation detection applications, there have been solutions proposed for this problem that may consist of establishing arrangements of photosensitive cell matrices organized along lines and columns, but with all four corers cut (essentially octagonal in shape) have been proposed. Some of these solutions only work with CCD type detector devices (charge-coupled Devices) where the period of the detector matrix is essentially larger than the minimum space necessary for placement of the addressing electronics, as is often true in intra-oral X-ray applications. In CCD technology there is no need for addressing along lines strictly speaking. Instead of a system of addressing along columns, the signal exiting a column is rather transferred along a readout register called "horizontal," from one column to the other. Thus, European Publication EP 1255401 proposes a solution for addressing a CCD type matrix designed for intra-oral applications with cut corners where line addressing passes through the horizontal readout register in an upper conductive layer. Such an embodiment remains limited to CCD type detectors and cannot be generalized to sensor matrices where each pixel must, for reading, be directly connected to a readout circuit, as is the case, for example, with detector matrices made using CMOS technology (Complementary Metal Oxide Semiconductor) allowing the realization of very small detector cells, of the order of some micrometers or even less than one micrometer, for the smaller pixels currently in use.

US Publication 2006027625 proposes another solution that can only be achieved through CCD technology for realizing an orthogonal matrix with obliquely cut corners, but which requires a readout register along the lines that can transfer the charges received from the obliquely cut columns to each time pulse of said column registers. This property is only available for CCD type detectors.

US Publication 20090033777 proposes a solution for a matrix of photosensitive cells addressed in lines and columns that may be achieved using CMOS technology, but it is limited to situations where the oblique sides are generally smaller than the orthogonal sides because the addressing blocks for either the lines or the columns on the oblique sides are placed behind the respective block on the orthogonal sides and are interconnected by a network of connections on the oblique sides. This network of interconnections in the context of a highly miniaturized application such as endoscopy, for example, may lead to an unwanted increase in the total surface.

Japanese Publication JP210273757 proposes an embodiment of the device comprising a matrix of generally circular shaped photodetector cells. However, it proposes maintaining the matrix of photoelectric cells in a rectangular or square shape, but using the space available along the centers of the orthogonal edges of the matrix for placement other electronic components necessary for the operation of a radiation detection system, specifically for capturing a highly integrated image. In another variation of this proposal, it is suggested to resolve the problem of addressing and readout in the matrix by placing a second electronic readout element in a second integrated circuit plane and interconnect the matrix of photodetector cells using 3D integration with the readout circuit. This considerably raises per unit production costs. The process of placing such a device on a production plate is limited to hexagonal shapes and if the plate is cut using a rectilinear sawing process, it generates a greater than 50% loss of potential surface on a production plate, such that the production cost for such a device is vastly increased. An alternative sawing process might consist of circular cutting, which is not a standard procedure for wide scale production of electronics.

French Publication No. 2 930 841 describes a device comprising a set of electromagnetic radiation-sensitive detectors for endoscopic applications with a configuration similar to the device described. However, the arrangement and the geometry of the addressing circuits differ and it does not offer the same advantages. More specifically, the device described in this publication requires an increased number of transistors to be integrated within each pixel, which is undesirable in the context of an endoscopic application where the size of each pixel is advantageously kept as small as possible in order to increase resolution in a detector with a reduced surface.

SUMMARY OF THE INVENTION

The present invention proposes to furnish an architecture permitting the manufacture of electromagnetic radiation-sensitive devices, specifically image sensors, with a matrix optimally covering the quasi-totality of the circular surface corresponding to the visual field of the lens and a sensor device adapted to this geometry, said sensor arrangement being associated with an addressing system for identifying the image points with no ambiguity by attributing a unique line address and column address to each photodetector cell. Thus they can be read in the conventional sequential way. However, the architecture proposes a means for placing line and address decoder elements along the edges that are oblique, relative to the rectilinear direction of the lines and columns in a conventional addressing scheme, with no limitation on the number of cut corners in said matrix.

In addition, the present invention can be generalized to all principles of photosensitive detector matrices, which require for reading a direct connection to one or more readout circuits, specifically image sensors made using CMOS technology. The principles proposed in the invention are compatible with the miniaturized size of radiation detector cells and may be applied to matrices with a period as small as from 1 to 2 micrometers. By proposing a unique solution for the placement and routing of circuits for addressing lines and columns along the oblique edges of said matrix without increasing additional space beyond the matrix of the detector cells necessary on the oblique edges of said addressing device.

For this purpose, the sensor of the invention as defined in the description is characterized in that the addressing circuits for lines or columns are alternately layered relative to the addressing circuits for columns or lines along said at least one oblique edge, said addressing circuits being arranged parallel to one another and generally perpendicular to said at least one oblique edge, and in that the width of a pair of addressing circuits consisting of a line and a column leading to a photodetector cell obliquely cut on said oblique edge is equal to the length of the diagonal of said photodetector cell obliquely cut on said oblique edge.

According to an advantageous embodiment in which said photodetector cells are square and said at least one oblique edge is cut at 45°, the width of one of said addressing circuits may be generally equal to $\sqrt{2}/2$ multiplied by the dimension of one side of a photovoltaic cell. The length of the circuits in this case is generally equal to the length of the circuits corresponding to the length of the straight sides multiplied by $\sqrt{2}$.

According to a particular embodiment said closed line is circular or oval in shape.

Advantageously, according to a particular embodiment, the polygonal shape of the matrix of photodetector cells is an octagon within a circle or an ellipse.

The elements for addressing the orthogonal lines and columns corresponding to the matrix of image points on the sensor may comprise means for addressing the lines and columns, said means comprising elements disposed along at least one portion of the sides of the polygonal outline of said matrix.

According to a particular embodiment, the elements of said addressing means for addressing lines and columns alternate along at least one oblique edge of said sensor's matrix of image points.

According to another particular embodiment the elements of said means for addressing lines and columns are disposed behind one another along at least one oblique edge of said sensor's matrix of image points.

According to yet another particular embodiment, the elements of said means for addressing lines and columns disposed along at least one oblique edge of the matrix of image points are narrower than the elements disposed along an orthogonal edge of said sensor's matrix of image points.

According to yet another particular embodiment, the elements of said means for addressing lines and columns are disposed along all the edges of the matrix, dividing the addressing of lines and columns between opposing edges across the matrix.

The image sensor advantageously may be mounted on a generally circular endoscopic tube and associated with an optical system comprising at least one circular lens.

The arrangement of the invention is characterized in that said assembly of devices is made on a production plate where said devices are octagonal in shape and where they are spaced in such a way that they can be cut apart using only straight lines that form only 45 degree angles with one another.

BRIEF DESCRIPTION OF THE DRAWINGS

The present invention and its advantages will be more understandable from reading the detailed description of preferred embodiments of the device with reference to the attached drawings given by way of non-limiting example, in which.

DETAILED DESCRIPTION OF THE PREFERRED EMBODIMENTS

Figure 1:
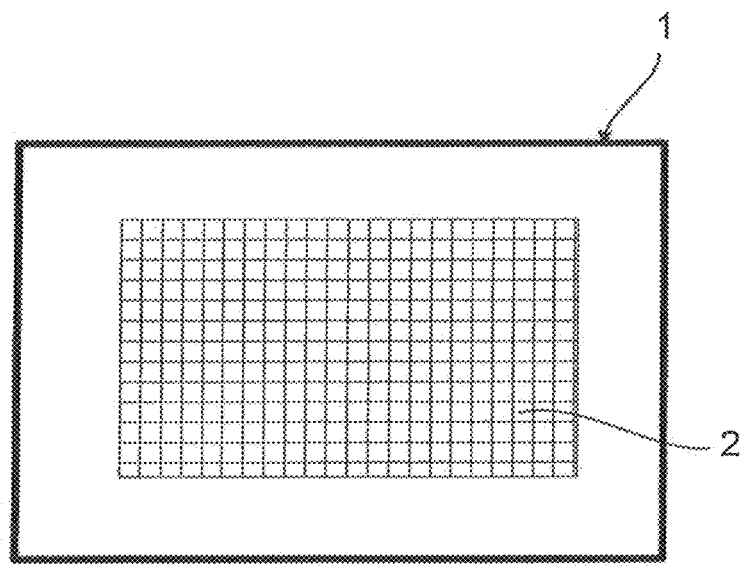
FIG. 1 represents a plane view illustrating a prior art matrix of photodetector cells.
Figure 2:
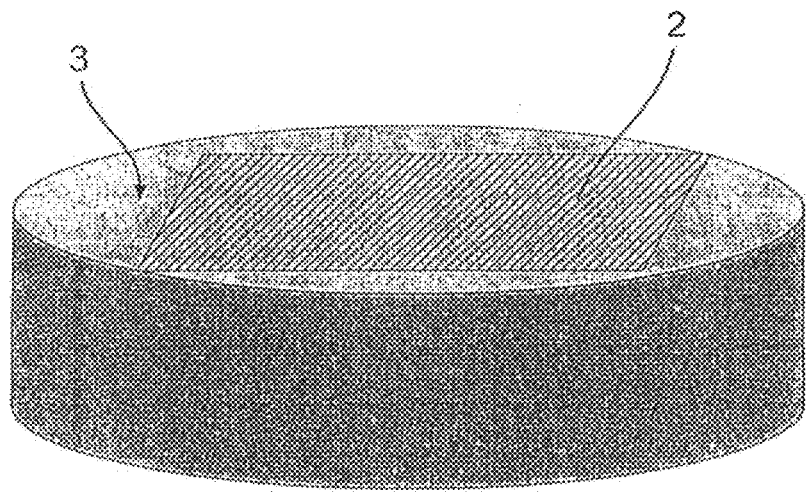
FIG. 2 represents a perspective view of the matrix of photodetector cells of FIG. 1 arranged on a circular support.

With reference to FIG. 1, a prior art cell photodetector is usually rectangular or square in shape and the cells form a matrix 2 of image points that are also rectangular or square. As shown in FIG. 2, this sensor is generally mounted on a support 3 that may be a circular shape endoscopic tube and the optical system associated with the sensor, which comprises one or more lenses, is typically circular.

Figure 3:
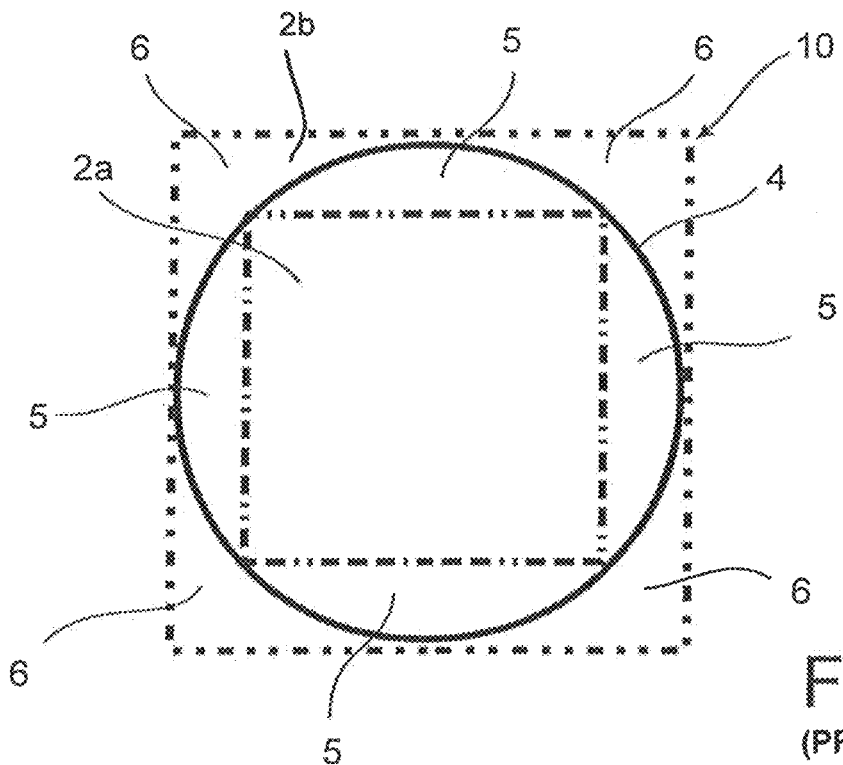
FIG. 3 represents a view illustrating the problem encountered when using a prior art matrix of photodetector cells and a circular lens.

The view in FIG. 3 shows the respective surfaces covered by a matrix 10 of prior art photodetector cells which is square, for example, and lens 4 of the optical system, circular in shape. According to a first embodiment matrix 2a is contained in a circle representing lens 4. In this case zones 5 which are outside matrix 2a and inside the circular contour of lens 4 are not covered by this lens and cannot furnish any image. According to a second embodiment the circle representing lens 4 is contained within matrix 2b. In this case zones 6 which are inside matrix 2b and outside the circular contour of lens 4 are not covered by said lens and cannot furnish any image. Therefore, this is not an optimal situation, and it is one which the present invention proposes to correct.

Figure 4:
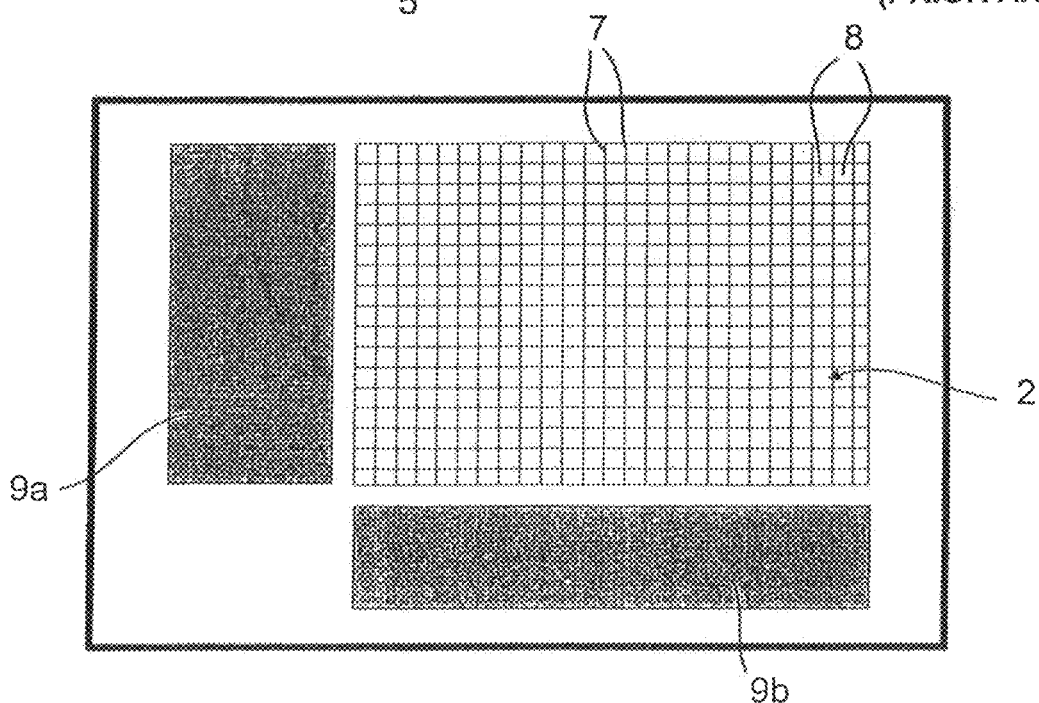
FIG. 4 illustrates the mode of addressing associated with a prior art matrix of photodetector cells.

FIG. 4 illustrates the addressing mode of a conventional prior art sensor with a matrix of image points arranged along lines 7 and columns 8 that are orthogonal relative to these lines. The addressing means comprises two elements 9a and 9b respectively impinging on lines 7 and columns 8 of photodetector cell matrix 2.

Figure 5:
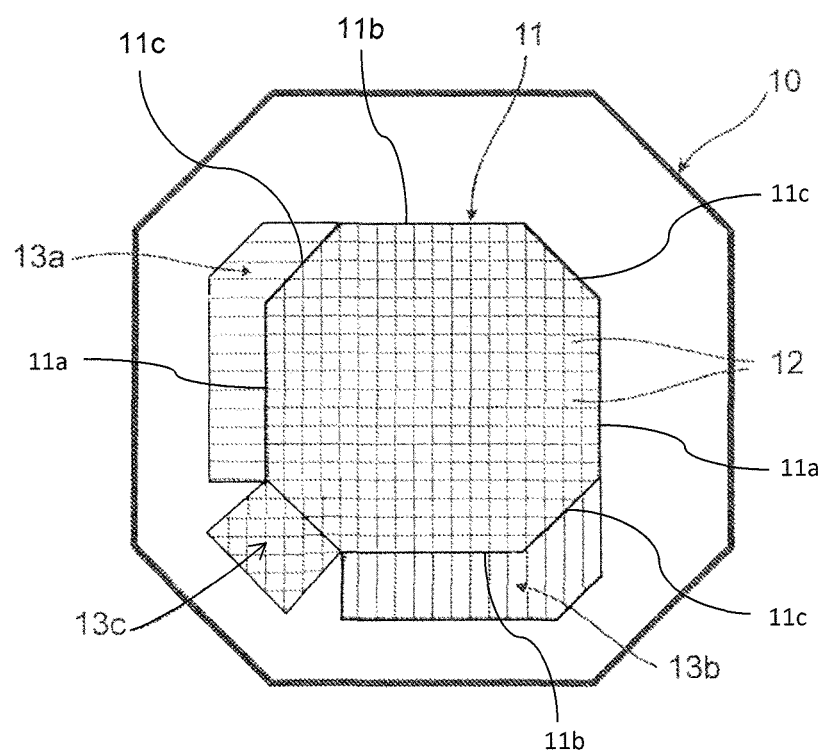
FIG. 5 illustrates an embodiment of a matrix of photodetector cells according to the invention associated with a specific addressing device.

FIG. 5 illustrates a sensor 10 according to the invention that comprises a matrix 11 of photodetector cells 12, said matrix 11 being octagonal in shape, and located along a periphery 11a, 11b of the matrix 11, output circuits 13a, 13b, 13c. To ensure complete addressing of the image points of matrix 11 of photodetector cells 12, it is necessary to place on at least one of the oblique sides 11c of the matrix at least one line addressing circuit 13a as well as at least one column addressing circuit 13b on the same oblique side 11c of the matrix, forming at least one set of juxtaposed circuits 13c. In this way extinguishment of the addressing circuit beyond the matrix does not increase significantly so that the benefit obtained by using a polygonal matrix of image points, for example, octagonal is substantial and allows an overall reduction of the sensor surface. The benefit of this arrangement is the fact that the periphery of a cell in the matrix of image points connected non-orthogonally increases according to Pythagorean laws, whereas the dimension of the unitary cell in the line decoder and the column decoder, respectively, does not increase if subjected to rotation.

Figure 6:
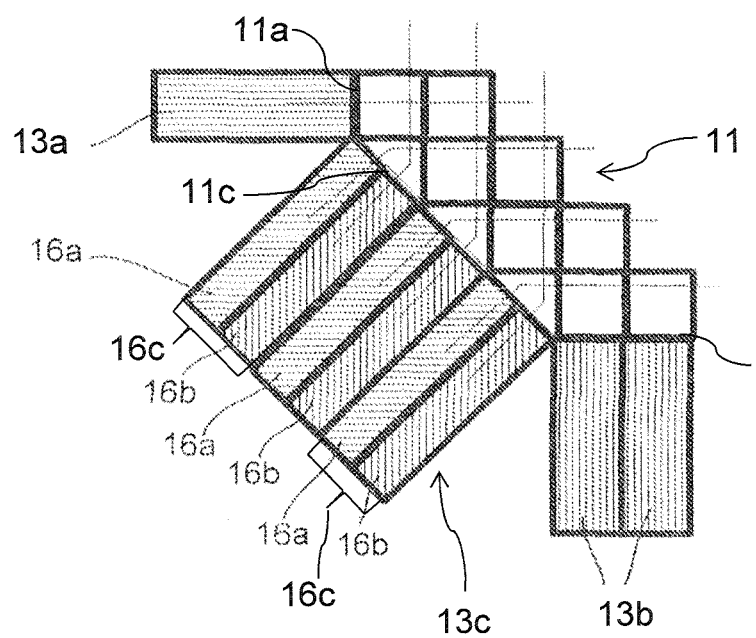
FIG. 6 is a partial view illustrating an embodiment of a specific mode of addressing adapted to the matrix of photodetector cells of FIG. 5.

This increase in the periphery of a unitary cell on the oblique sides of the matrix of photodetector cells is used for placing a base element of the line and column addressing means. FIG. 6 shows the components of the integrated circuit of the line addressing circuits 16a and the column addressing circuits 16b that are arranged side by side, together forming at least one set of juxtaposed circuits 16c, on the oblique side 11c of a matrix with a side angled at 45° relative to the lines and columns. In this case the width of a pair of said addressing circuits 16c is generally equal to the dimension of one side of a photodetector cell multiplied by $\sqrt{2}$, perhaps about 1.4. This increase in dimension is used for the layered placement of the addressing circuits for the lines and columns.

Figure 7A:
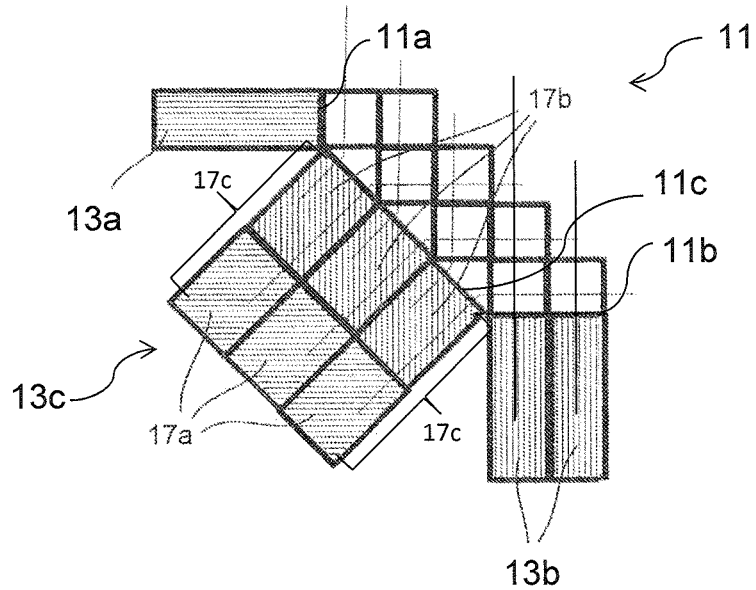
FIGS. 7A and 7B are partial views illustrating other specific modes of addressing adapted to the matrix of photodetector cells of FIG. 5.
Figure 7B:
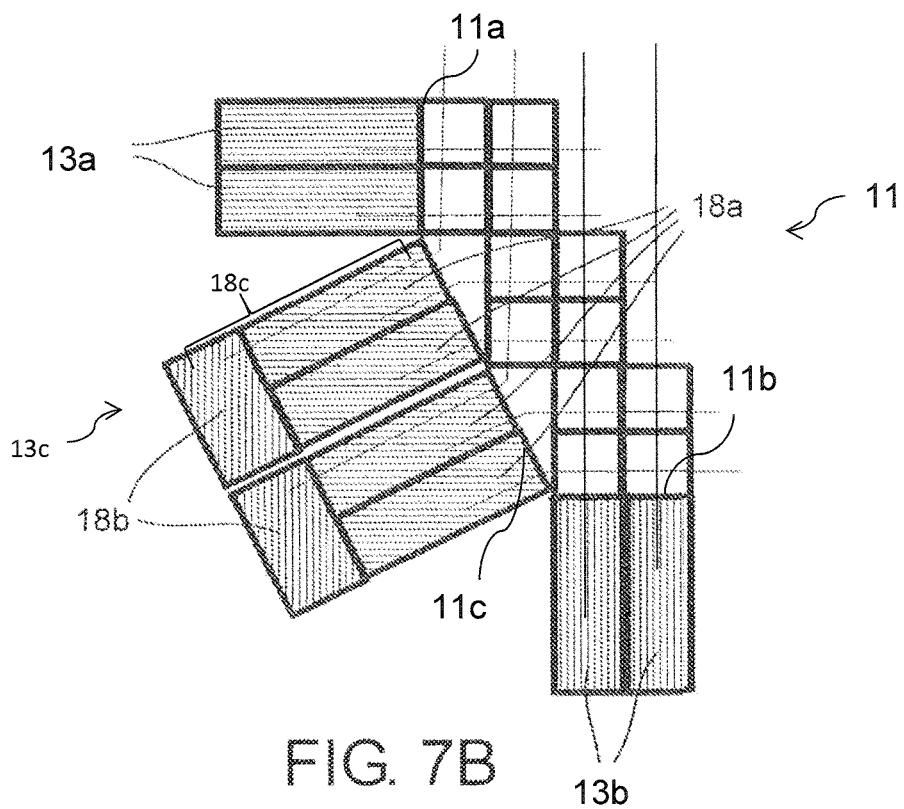

Other configurations are illustrated in FIGS. 7A and 7B. In the case of the configuration shown in FIG. 7A, the extinguishment of lines and columns beyond the matrix may be reduced because of the larger width of the base elements of the means for addressing lines 17a located behind the base elements for the means for addressing columns 17b, together forming at least one set of juxtaposed circuits 17c along the at least one oblique side 11c. The reverse arrangement is also possible.

This concept can be extended to polygonal contours of matrices with side angles other than 45°. FIG. 7B describes such a configuration where a sufficient number of base elements for the means of addressing lines and columns are placed in each section of the periphery 11a, 11 b of the matrix of image points. The oblique side of the matrix of FIG. 7B has a 26° angle. Two base elements for the means of addressing lines 18a are interposed between one base element for the means of addressing columns 18b, together, all three forming one set of juxtaposed circuits 18c along the at least one oblique side 11c of the matrix 11.

According to a variation of the sensor of the invention, the addressing circuits for the lines and columns are distributed along all sides of the matrix so that certain groups of lines of image points are addressed on one side, while certain other groups of lines of image points are addressed on the opposite side, and likewise for the columns. For example, even lines may be addressed on the far left side of the matrix of image points, while odd lines may be addressed on the far right of the matrix of image points. The same may be true for even and odd columns on the lower or upper edges of the matrix of image points that may be selected for positioning respective addressing circuits.

Thus, by using the principles described above, it is possible to achieve an image sensor comprising a polygonal shaped matrix, for example, octagonal, or even decagonal to approximate a circular shape by increasing the number of sides, but also permitting the entire image sensor with the electronic circuits to cover a polygonal surface.

During industrial scale production of an electronic circuit, especially an image sensor with a non-rectangular shape, particularly polygonal, or octagonal, for example, the question arises of separating individual circuits from the panels on which a plurality of circuits are manufactured, bearing in mind that the methods for separating electronic circuits are based on the principle of cutting or sawing in a straight line.

Figure 8:
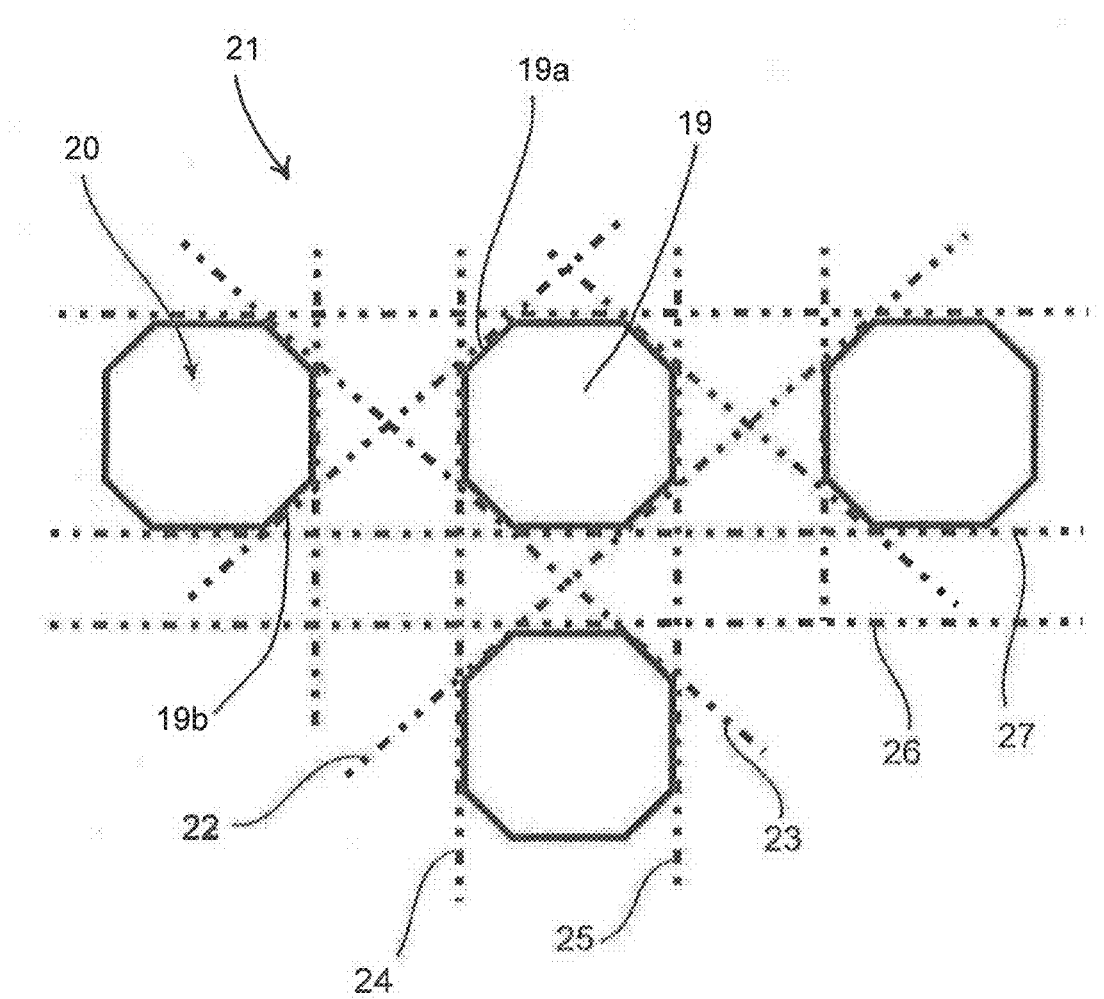
FIG. 8 is a schematic view illustrating a mode of industrial fabrication of a series of photodetector cell matrices for producing sensors according to the invention.

By way of example, FIG. 8 illustrates the manufacturing of polygonal panels initially in an arrangement comprising a plurality of octagonal shaped image sensors 20 on a production panel 21 such that they can be cut apart along cutting lines 22, 23 which cross at 90°, and parallel cutting lines 24, 25 and 26, 27. It is necessary only to place the octagonal circuits 19 in spaced lines and columns. Cutting can be done in such a way that the side represented in the upper left 19a of a circuit represented in the drawing corresponds to the lower right side 19b of another circuit.

The present invention is not limited to the embodiments described, but may undergo various modifications or variations obvious to a person skilled in the art. In particular, the number of sides is limited only by practicalities. The shape is adaptable and the addressing means are elaborated as a function of the geometric shape of the image matrices.

The invention claimed is:

1. An image sensor, designed to furnish an image of an explored area that generally corresponds in shape to a geometry of the sensor, the sensor comprising:
    a matrix of photodetector cells being electromagnetic radiation-sensitive detector cells;
    the matrix of photodetector cells having an outline being polygonal in shape;
    the matrix of photodetector cells having a periphery with at least one oblique edge connecting two orthogonal edges together with one another;
    each of the photodetector cells being directly connected to one of a plurality of line addressing circuits and one of a plurality of column addressing circuits of a readout circuit;
    each of the plurality of line addressing circuits and the plurality of column addressing circuits of the readout circuit being located along the periphery of the matrix of photodetector cells; and
    wherein the readout circuit is arranged along the at least one oblique edge; and
    along the at least one oblique edge, at least one of the plurality of line addressing circuits is juxtaposed with at least one of the plurality of column addressing circuits.

2. The sensor according to claim 1, wherein the geometry of the sensor is circular in shape, and the periphery of the matrix of photodetector cells having a plurality of oblique edges such that the shape of the outline of the matrix of photodetector cells approaches the geometry of the sensor.

3. The sensor according to claim 1, wherein the geometry of the sensor is oval in shape, and the periphery of the matrix of photodetector cells having a plurality of oblique edges such that the shape of the outline of the matrix of photodetector cells approaches the geometry of the sensor.

4. The sensor according to claim 1, wherein the sensor is mounted on an endoscopic tube having a circular cross section and the sensor is associated with an optical system and located on a circular lens.

5. The sensor according to claim 1, wherein the sensor is made using Complementary Metal Oxide Semiconductor technology.

6. The sensor according to claim 1, wherein the sensor is manufactured as a set of sensors;
    the set of sensors is manufactured on a production pallet;
    each of the sensors are octagonal in shape; and
    each of the sensors are placed and spaced on the production pallet such that straight cutting lines form 45° angles with one another.

7. The sensor according to claim 1, wherein a presentation format of the image is based on an image point matrix which is arranged in lines and columns corresponding to line addressing circuits and the column addressing circuits of the readout circuit.

8. The sensor according to claim 1, wherein each of the photodetector cells of the matrix are square and have a cell length;
    an angle between the at least one oblique edge and a first of the two orthogonal edges is 45°;
    first sides of the at least one of the line addressing circuits and the at least one of the column addressing circuits are directly adjacent the at least one oblique edge;
    the first sides both have a length equal to $\sqrt{2}/2$ multiplied by the cell length;
    second sides of the at least one of the line addressing circuits and the at least one of the column addressing circuits are both perpendicular to the at least one oblique edge; and
    the second sides are directly adjacent one another.

9. The sensor according to claim 1, wherein each of the photodetector cells of the matrix are square and have a cell length;
    an angle between the at least one oblique edge and a first of the two orthogonal edges is 45°;
    first sides of the at least one of the line addressing circuits and the at least one of the column addressing circuits are directly adjacent one another;
    second sides of the at least one of the line addressing circuits and the at least one of the column addressing circuits are parallel to the first sides;
    the first and the second sides both have a length equal to $\sqrt{2}$ multiplied by the cell length; and
    only the second sides of the at least one of the line addressing circuits are directly adjacent the at least one oblique edge.

10. The sensor according to claim 1, wherein each of the photodetector cells of the matrix are square and have a cell length;
    an angle between the at least one oblique edge and a first of the two orthogonal edges is 26°;
    a first side of the at least one of the column addressing circuits has a length equal to $\sqrt{5}/2$ multiplied by the cell length;
    a first side of the at least one of the line addressing circuits has a length equal to $\sqrt{5}$ multiplied by the cell length;
    first sides of the at least one of the line addressing circuits and the at least one of the column addressing circuits are directly adjacent one another;
    a second side of the at least one of the column addressing circuits is directly adjacent the at least one oblique edge.

11. An image sensor comprising:
    a matrix of photodetector cells having at least one oblique edge connecting two orthogonal edges together;
    a readout circuit being located along the two orthogonal edges and the at least one oblique edge of the matrix of photodetector cells;
    the readout circuit having a plurality of line addressing circuits and a plurality of column addressing circuits; and
    each of the photodetector cells of the matrix being directly connected to one of the plurality of line addressing circuits and one of the plurality of column addressing circuits of the readout circuit;
    wherein, at least one set of juxtaposed circuits of the readout circuit is located along the at least one oblique edge.

12. The sensor according to claim 11, wherein the sensor is manufactured as a set of sensors;
the set of sensors is manufactured on a production pallet;
each of the sensors are octagonal in shape; and
each of the sensors are placed and spaced on the production pallet such that straight cutting lines form 45° angles with one another.

13. The sensor according to claim 11, wherein a presentation format of the image is based on an image point matrix which is arranged in lines and columns corresponding to the plurality of line addressing circuits and the plurality of column addressing circuits of the readout circuit.

14. The sensor according to claim 11, wherein each of the photodetector cells of the matrix are square and have a cell length;
an angle of 45° is between the at least one oblique edge and a first edge of the two orthogonal edges;
the at least one set of juxtaposed circuits along the at least one oblique edge comprises at least one of the plurality of line addressing circuits and at least one of the plurality of column addressing circuits;
first sides of at least one of the plurality of line addressing circuits and at least one of the plurality of column addressing circuits are directly adjacent the at least one oblique edge;
the first sides both have a length equal to $\sqrt{2}/2$ multiplied by the cell length;
second sides of at least one of the plurality of line addressing circuits and at least one of the plurality of column addressing circuits are both perpendicular to the at least one oblique edge; and
the second sides are directly adjacent one another.

15. The sensor according to claim 11, wherein each of the photodetector cells of the matrix are square and have a cell length;
an angle of 45° is between the at least one oblique edge and a first of the two orthogonal edges;
the at least one set of juxtaposed circuits along the at least one oblique edge comprises at least one of the plurality of line addressing circuits and at least one of the plurality of column addressing circuits;
first sides of at least one of the plurality of line addressing circuits and at least one of the plurality of column addressing circuits are directly adjacent one another;
second sides of at least one of the plurality of line addressing circuits and at least one of the plurality of column addressing circuits are parallel to the first sides;
the first and the second sides both have a length equal to $\sqrt{2}$ multiplied by the cell length; and
only first sides of at least one of the plurality of line addressing circuits are directly adjacent the at least one oblique edge.

16. The sensor according to claim 11, wherein each of the photodetector cells of the matrix are square and have a cell length;
an angle of 26° is between the at least one oblique edge and a first of the two orthogonal edges;
the at least one set of juxtaposed circuits along the at least one oblique edge comprises at least two of the plurality of line addressing circuits and at least one of the plurality of column addressing circuits;
a first side of the at least one of the plurality of line addressing circuits has a length equal to $\sqrt{5}$ multiplied by the cell length;
a first side of each of the at least two of the plurality of column addressing circuits has a length equal to $\sqrt{5}/2$ multiplied by the cell length;
the first sides of the at least one of the plurality of line addressing circuits and the at least two of the plurality of column addressing circuits are directly adjacent one another;
a second side of each of the at least two of the plurality of column addressing circuits is directly adjacent the at least one oblique edge; and
a third side of each of the at least two of the plurality of column addressing circuits are directly adjacent one another.

17. An image sensor, for generating an image based upon electromagnetic radiation detected, the sensor comprising:
a matrix of photodetector cells being electromagnetic radiation-sensitive detector cells;
the matrix of photodetector cells having a shape corresponding to an outline of the sensor,
the outline of the sensor being polygonal in shape and having at least five sides within a closed outer peripheral line;
a readout circuit located along two orthogonal edges and at least one oblique edge connecting the two edges being together with one another along a periphery of the matrix of photodetector cells;
the readout circuit having a plurality of line addressing circuits and a plurality of column addressing circuits;
each of the photodetector cells of the matrix being directly connected to only one of the plurality of line addressing circuits and only one of the plurality of column addressing circuits of the readout circuit, such that each of the photodetector cells of the matrix have a unique address corresponding to lines and columns of an addressing scheme; and
the addressing scheme corresponding to an image point matrix being a basis for a presentation format of the image;
wherein, along the at least one oblique edge, each one of the plurality of line addressing circuits is juxtaposed with a respective one of the plurality of column addressing circuits; and
each of the photodetector cells associated with the at least one oblique edge is respectively connected to the one of the plurality of line addressing circuits and the one of the plurality of column addressing circuits.

* * * * *